(12) United States Patent
Craig et al.

(10) Patent No.: US 10,262,560 B2
(45) Date of Patent: Apr. 16, 2019

(54) TOOTH WHITENING STRIP ARTICLE PRODUCTS WITH WHITENING POWER INDEX

(71) Applicant: The Procter & Gamble Company, Cincinnati, OH (US)

(72) Inventors: Stephanie Tich Craig, Loveland, OH (US); John B. Maitrejean, Hummelstown, PA (US); James Radley, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 207 days.

(21) Appl. No.: 15/066,013

(22) Filed: Mar. 10, 2016

(65) Prior Publication Data
US 2016/0189572 A1 Jun. 30, 2016

Related U.S. Application Data

(62) Division of application No. 13/604,913, filed on Sep. 6, 2012.

(60) Provisional application No. 61/531,501, filed on Sep. 6, 2011.

(51) Int. Cl.
| | |
|---|---|
| *G06F 19/00* | (2018.01) |
| *G01N 31/00* | (2006.01) |
| *G09F 3/00* | (2006.01) |
| *A61K 8/38* | (2006.01) |
| *A61Q 11/00* | (2006.01) |
| *A61K 8/22* | (2006.01) |
| *A61K 8/02* | (2006.01) |

(52) U.S. Cl.
CPC .............. *G09F 3/00* (2013.01); *A61K 8/0204* (2013.01); *A61K 8/22* (2013.01); *A61K 8/38* (2013.01); *A61Q 11/00* (2013.01); *A61K 2800/10* (2013.01); *A61K 2800/87* (2013.01); *B65D 2203/00* (2013.01)

(58) Field of Classification Search
None
See application file for complete search history.

(56) References Cited

U.S. PATENT DOCUMENTS

2004/0219111 A1* 11/2004 Kim ...................... A61K 8/0208
424/49
2004/0258723 A1* 12/2004 Singh ................... A61C 19/063
424/401

(Continued)

*Primary Examiner* — David M. Gray
*Assistant Examiner* — Geoffrey T Evans
(74) *Attorney, Agent, or Firm* — Parker D. McCrary

(57) ABSTRACT

Tooth-whitening strip articles, packages, arrays and methods including one or more tooth-whitening strip articles having a power configuration corresponding to a consumer desirable level of treatment, the tooth-whitening strip articles being enclosed in a package; a brand indicator disposed on the package; a line-up indicator disposed on the package, the line-up indicator including at least one line-up indicia selected from visual indicia, narrative indicia or combinations thereof; and optionally, a power specific indicator disposed on the package; wherein the line-up indicator associates the tooth-whitening strip article configuration with a corresponding whitening power, the association enabling a consumer to identify the appropriate tooth-whitening strip article configuration for a user.

3 Claims, 6 Drawing Sheets

(56) References Cited

U.S. PATENT DOCUMENTS

| | | | |
|---|---|---|---|
| 2005/0074723 A1* | 4/2005 | Ostler | A61C 17/20 433/216 |
| 2005/0163729 A1* | 7/2005 | Zaidel | A61K 8/19 424/53 |
| 2005/0281757 A1* | 12/2005 | Ibrahim | A61K 8/0208 424/49 |
| 2007/0183988 A1* | 8/2007 | Prosise | A61K 8/22 424/53 |
| 2007/0218015 A1* | 9/2007 | Hardy | A61K 8/0208 424/49 |
| 2013/0004912 A1* | 1/2013 | Brown | A61C 17/20 433/86 |

* cited by examiner

TOOTH WHITENING STRIP ARTICLE PRODUCTS WITH WHITENING POWER INDEX

CROSS REFERENCE TO RELATED APPLICATION

This application is a Divisional of U.S. application Ser. No. 13/604,913, filed Sep. 6, 2012; which claims the benefit of U.S. Provisional Application No. 61/531,501, filed Sep. 6, 2011.

FIELD OF THE INVENTION

The present invention relates to tooth-whitening strip articles and improved communication to consumers on the packaging therefore.

BACKGROUND OF THE INVENTION

Consumer oral care whitening products such as tooth-whitening strips are designed to improve the overall appearance of teeth. The tooth-whitening strips typically include a backing layer (such as a polymeric material) in combination with a whitening composition (such as those containing peroxide). Such products are designed to be applied to the tooth surface for a period of time to reduce surface stains on the tooth enamel and thereby reduce the appearance of such stains. Multiple products are on the market and are variable in their efficacy due to such factors as the level of peroxide in the composition, the size of the strip, the recommended wearing time, the recommended frequency of wear, the number of strips provided in a given package, and the like.

Because of the varying factors from one product to the next, consumers have a difficult time selecting a particular packaged product to meet their individual tooth-whitening needs. For instance, a consumer that desires a low level of whitening, such as a consumer that has had professional whitening in the past or a more comprehensive at-home treatment, may be looking for a tooth-whitening strip packaged product that will provide simply a "touch-up". Such a desire for a "touch-up" may result from frequent drinking of beverages such as coffee, that have slightly stained the tooth surface. On the other hand, for instance, a consumer that is using a whitening product for the very first time, may want to have a more intensive whitening treatment.

Further complicated the consumer selection of the appropriate tooth-whitening strip product is that a particular level of whitening efficacy could be reached in a variety of ways such as by varying such factors as the level of peroxide in the composition, the size of the strip, the recommended wearing time, the recommended frequency of wear, the number of strips provided in a given package, and the like. For instance, a product that contains a higher level of peroxide that is sold with instructions to use for a shorter period of time might provide the same level of eventual whitening efficacy as a product with a lower level of peroxide that is sold with instructions to use more frequently and/or for longer periods of time per wear. At the same time, a person with, for instance, sensitive gum tissues may prefer to select a longer period of time with a lower level of peroxide to reach their desirable benefit.

Although providing a variety of tooth-whitening strip designs to consumers may meet a consumer need, a consumer given an overwhelming range of options may select the wrong product (i.e., a product other than that intended) or a product which may not be optimum (i.e., wrong number of strips, wrong whitening efficacy, too long of wear time). Either could lead to a less than ideal user experience.

Thus, there remains a need for tooth-whitening strip articles and arrays of tooth-whitening strip articles, that make it easier for a consumer to select a design from a variety of configurations that matches a particular user's needs.

SUMMARY OF THE INVENTION

It has now been surprisingly found that by calculating a whitening power level and indexing the whitening power level against other possible whitening power levels, that such information can be provided to consumers along with other information on the package of a tooth-whitening strip product to better communicate the appropriate product configuration to meet the needs and/or desires of the consumer user.

The foregoing articles, packages, arrays, systems and methods can be employed relative to tooth tooth-whitening strips having a range of whitening efficacies and a variety of designs or configurations.

BRIEF DESCRIPTION OF THE DRAWINGS

While the specification concludes with claims which particularly point out and distinctly claim the invention, it is believed the various embodiments will be better understood from the following description taken in conjunction with the accompanying drawings, in which:

The patent or application file contains at least one drawing executed in color. Copies of this patent or patent application publication with color drawing(s) will be provided by the Office upon request and payment of the necessary fee.

DETAILED DESCRIPTION OF THE INVENTION

As used herein, "visual indicia" is an identifying marking which may include any illustration, painting, photograph, drawing, picture, logo, hologram or graphic that visually communicates or signals characteristics of a product in use. In one embodiment, the visual indicia includes a sequence of graphical and/or pictorial representations corresponding to a whitening power index.

As used herein, "narrative indicia" is an identifying marking which may include letters, numbers or a combination thereof that communicates or signals characteristics of a product in use. In one embodiment, the narrative indicia comprises first indicia and second indicia, the first indicia corresponding to a first whitening power and the second indicia corresponding to a second whitening power, the first and second indicia being visibly different. In one embodiment, the first whitening power comprises a gentle whitening power. In another embodiment, the second whitening power comprises a professional power.

Discussed in more detail below are articles comprising one or more tooth-whitening strip articles having a power configuration corresponding to a consumer desirable level of treatment, the tooth-whitening strip articles being enclosed in a package; a brand indicator disposed on the package; a line-up indicator disposed on the package, the line-up indicator including at least one line-up indicia selected from visual indicia, narrative indicia or combinations thereof; and optionally, a power specific indicator disposed on the package; wherein the line-up indicator associates the tooth-whitening strip article configuration with a corresponding whitening power, the association enabling a consumer to identify the appropriate tooth-whitening strip article configuration for a user.

Further discussed in more detail below are packages including a front panel having a top and bottom portion; one or more tooth-whitening strip articles having a power configuration corresponding to a consumer desirable level of treatment, the tooth-whitening strip articles being enclosed in a package; a power communication system disposed on the top portion for associating the tooth-whitening strip article configuration with a corresponding whitening power, the association enabling a consumer to identify the appropriate tooth-whitening strip article configuration for a user; and an informational corridor disposed on the bottom portion, wherein the informational corridor includes at least two indicators selected from a number of treatments indicator, a number of strips indicator, a treatment time indicator, a product benefit indicator, and combinations thereof.

Figure 1:
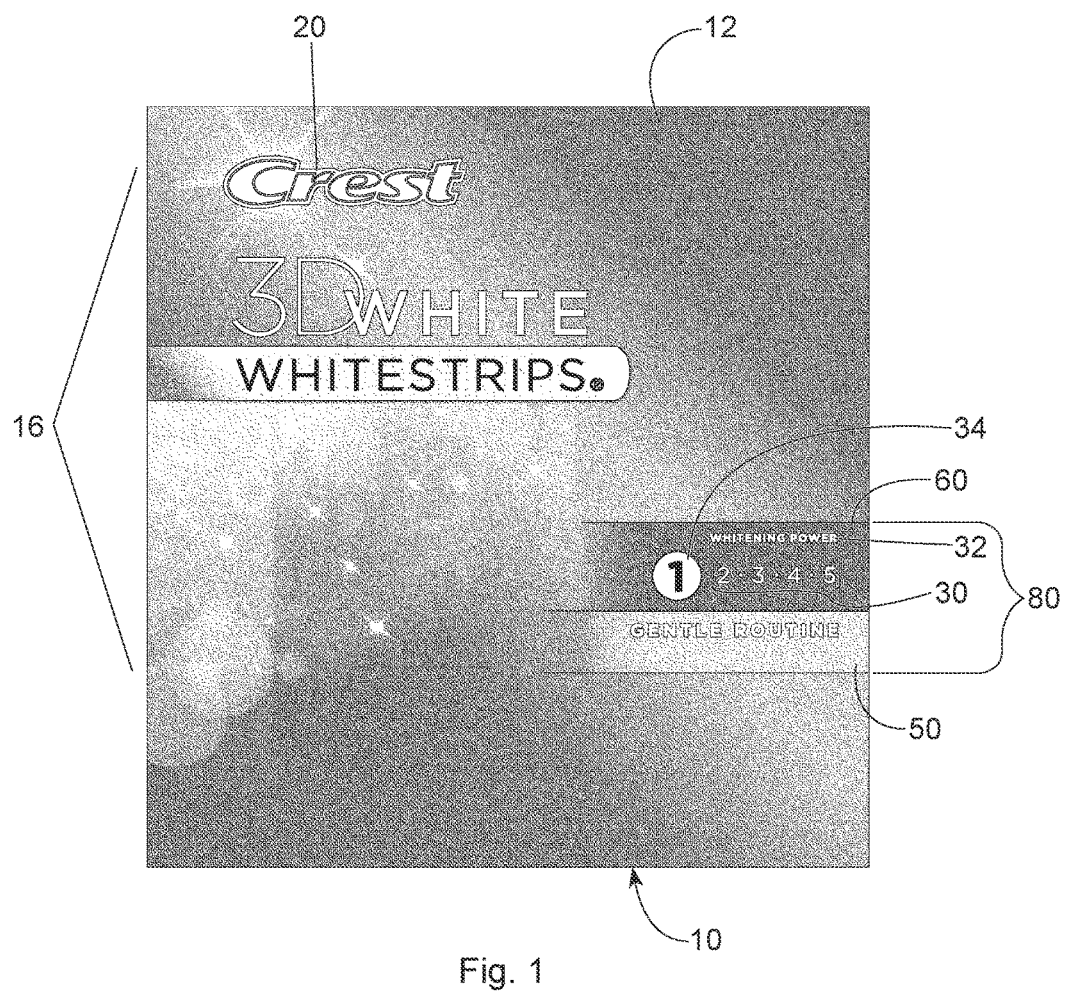
FIG. 1 illustrates an exemplary front panel of a package of tooth-whitening strip articles in accordance with one embodiment.

Referring to FIG. 1, package 10 includes a front panel 12 having a top and bottom portion and has one or more tooth-whitening strip articles (not shown) enclosed therein, a power communication system 16, and a line-up indicator 30. The line-up indicator 30 includes at least one line-up indicia selected from visual indicia, narrative indicia, or combinations thereof. The line-up indicator associates the tooth-whitening strip article configuration with a corresponding whitening power, the association enabling a consumer to identify the appropriate tooth-whitening strip article configuration for a user.

Figure 2:
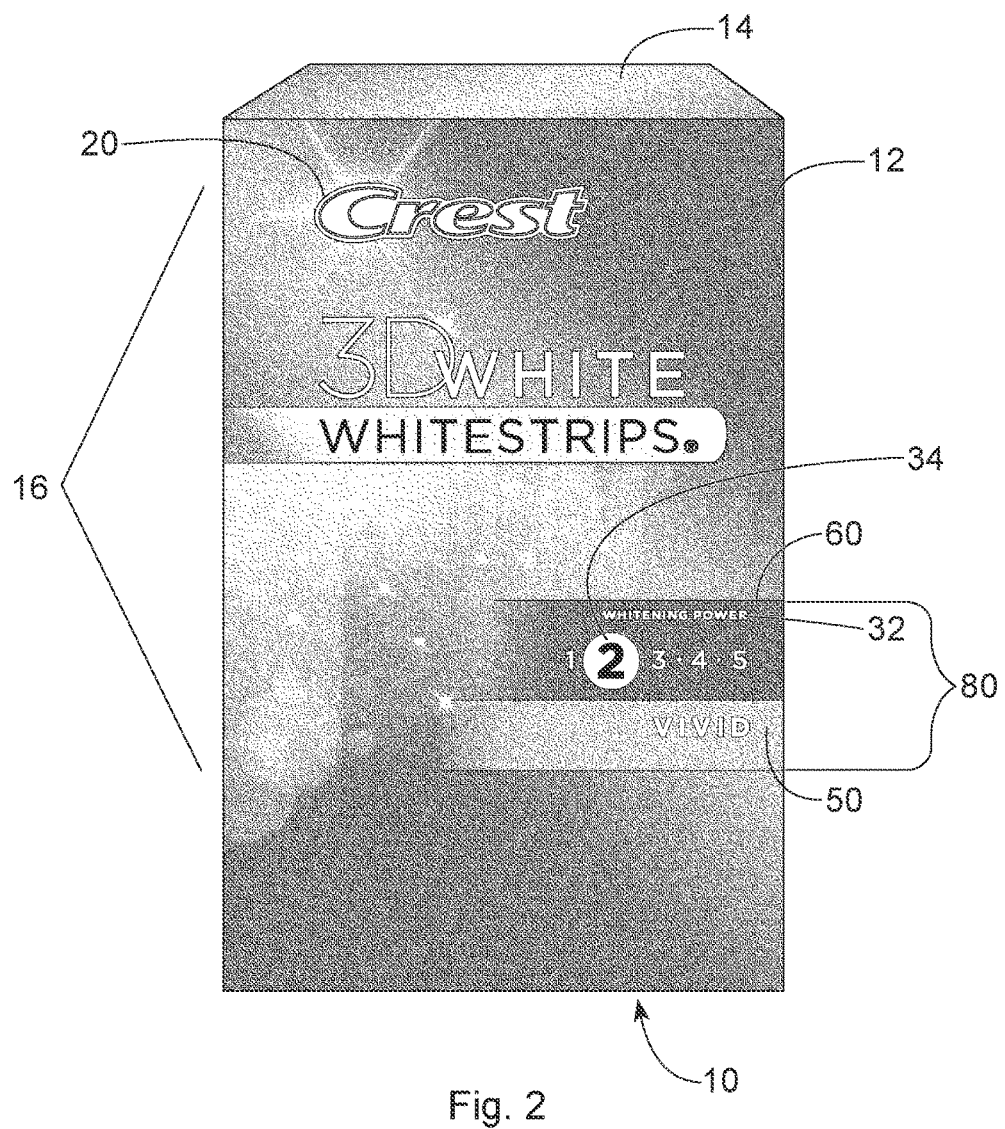
FIG. 2 illustrates an exemplary front panel of a package of tooth-whitening strip articles in accordance with one embodiment.

In one embodiment, the line-up indicator comprises narrative indicia 32 and visual indicia 34 each of these indicators disposed on the front panel 12. In one embodiment, the power communication system 16 includes a brand indicator 20, a line-up indicator 30 and a power specific indicator 50, each of these indicators disposed on the front panel 12. In another embodiment, the power communication system 16 is disposed on the bottom portion of the front panel 12. As described in more detail below, the power communication system 16 communicates both brand benefits and the line-up of tooth-whitening article configurations more clearly to consumers. Referring to FIG. 2, the package 10 includes an end panel 14.

The tooth-whitening strip articles can be packaged in a variety of containers such as bags, boxes or cartons. In one embodiment, as shown in FIG. 1, the tooth-whitening strip articles are packaged in a box. In another embodiment, the package 10 may be a plastic "shrink-wrap" container.

The package and array of tooth-whitening strip articles described herein may be applicable to a number of tooth-whitening strip products. The embodiments illustrated in FIGS. 1 2, 3, 4, and 5 include an assortment of tooth-whitening strip products made available in a variety product configurations where each configuration includes distinguishable characteristics comprising structural differences addressing a user's desired level of whitening. The levels of whitening may range from minor touch-ups to advanced or professional whitening strengths.

For example, the number of strips or number of treatments in a package may be selected from 1 to about 50, alternatively from about 1 to about 30, alternatively from about 1 to about 25, alternatively from about 1 to about 10.

Overlapping efficacy and eventual results expected from a tooth-whitening strip product make it difficult for a consumer to choose the right product configuration matching a particular consumer need. For this reason, an article is provided that facilitates consumers' selection of the appropriate product configuration from a variety of configurations.

Still referring to FIGS. 1 and 2, the brand indicator 20 includes a term corresponding to a brand of tooth-whitening strip article products. As used herein, the term "brand" refers to any term, symbol, design or combination thereof that identifies and differentiates a seller's product or service. The term "brand" also encompasses the set of expectations associated with a product or service which typically arise in the minds of consumers. In one embodiment, the brand indicator comprises a term corresponding to a brand of tooth-whitening strip article products. In one example, brand indicator 20 includes the term CREST. In another example, brand indicator 20 may include the term ORAL B. In another example, brand indicator 20 may include the term 3D WHITE. In another example, brand indicator 20 may include the term WHITESTRIPS. In another example, brand indicator 20 may include the term VIVID WHITE. Each of these brand indicators are trademarks of tooth-whitening strip article products manufactured by The Procter and Gamble Company, Cincinnati, Ohio, USA. In one embodiment, the brand indicator 20 may include a brand associated with a retailer such as WALGREENS, CVS, WALMART, RITE-AID, TARGET, or combinations thereof.

The line-up indicator 30 assists consumers in identifying the appropriate tooth-whitening strip article configuration for a particular user by associating each tooth-whitening strip article configuration with a corresponding whitening power. As shown in FIGS. 1-5, the line-up indicator 30 includes narrative indicia 32 and visual indicia 34 in order to convey the various whitening power levels to the consumer. In one embodiment, the narrative indicia 32 is located in a proximal relationship with the visual indicia 34. In one example, the narrative indicia 32 and the visual indicia 34 are arranged horizontally. In another example, the narrative indicia 32 and the visual indicia 34 might be arranged vertically.

Figure 3:
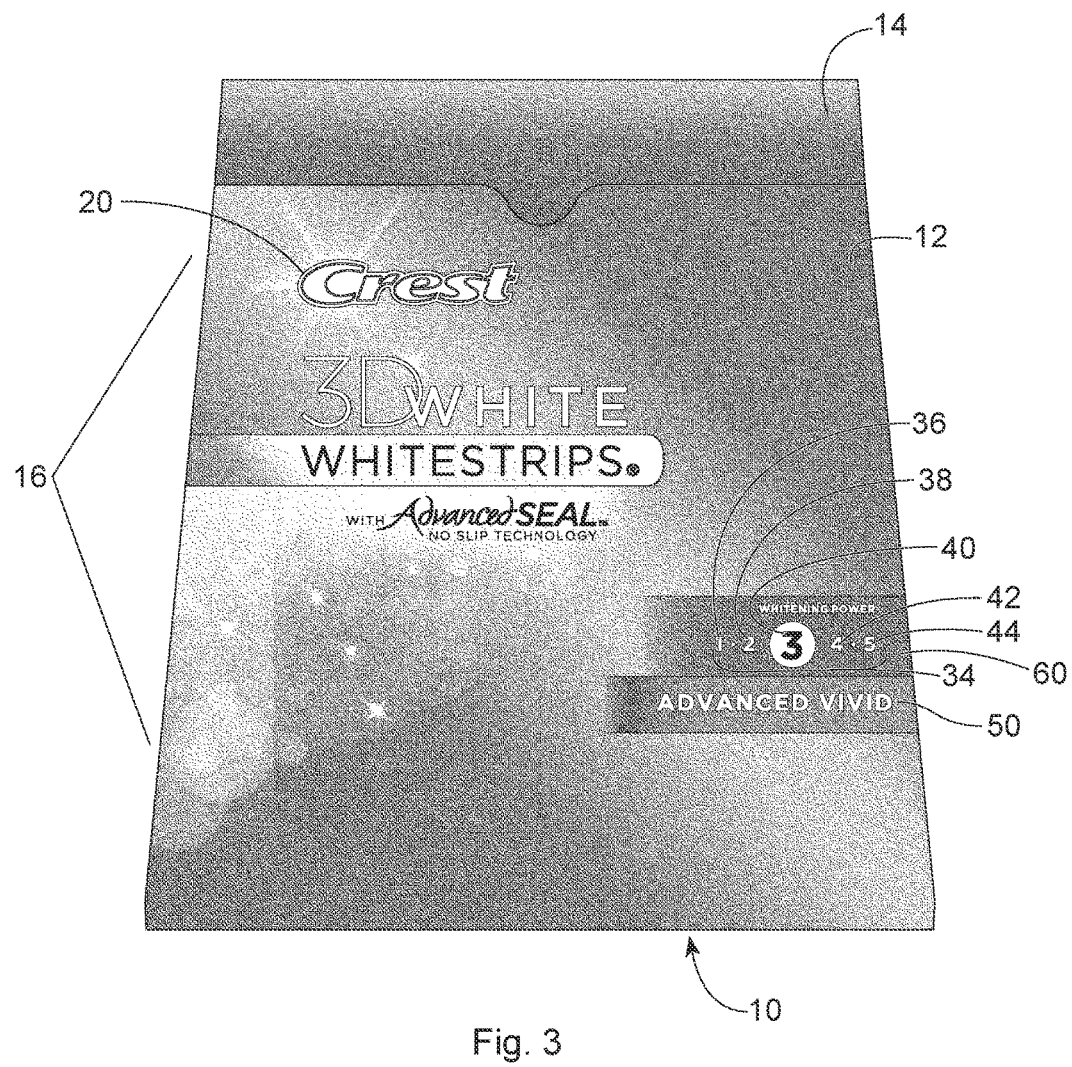
FIG. 3 illustrates an exemplary front panel of a package of tooth-whitening strip articles in accordance with one embodiment.

As further shown in FIG. 3, the visual indicia 34 may include a sequence of numbers or symbols corresponding to a user's desired level of whitening. In one embodiment, the visual indicia 34 includes five narrative indicia selected from Arabic numerals, each visibly different and each corresponding to a different level of whitening. For example, a first indicia 36 corresponding to the first level of whitening might be the number "1". A second indicia 38 corresponding to the second level of whitening might be the number "2". A third indicia 40 corresponding to the third level of whitening might be the number "3". A fourth indicia 42 corresponding to the fourth level of whitening might be the number "4". A fifth indicia 44 corresponding to the fifth level of whitening might be the number "5". As shown in FIG. 3, any of the indicia can be highlighted by increasing the size of one or more indicia relative to the rest and/or changing the color of the background behind one indicia relative to the rest and/or including a graphical design behind one indicia. By matching the level of whitening in the product, the level of whitening desired by the user and the level of whitening exhibited by the visual indicia 34, the consumer can choose the right product configuration for their particular use. While round or circular backgrounds to visual indicia 34 are shown in FIGS. 1-4, visual indicia of other shapes may also be used, if desired.

In another embodiment, the line-up indicator 30 may be provided on a display panel disposed above the store shelves on which the tooth-whitening strip article configurations are displayed for sale. In another embodiment, the line-up indicator 30 may be disseminated in electronic or print media. Electronic media includes internet, television, terrestrial and satellite radio or any media broadcast through electronic means. Printed media includes all forms of visual or sensory media not transmitted via electronic means, for example, magazines, billboards, store displays, flyers, inserts and newspapers. In another embodiment, the line-up indicator 30 may be disseminated in kiosks and 3-D displays. Kiosks and 3-D displays can be interactive and can incorporate media to provide multiple avenues for disseminating visual and narrative indicia to the consumer simultaneously.

In the embodiment shown in FIGS. 1-5, the sequence of icons or indicia are located adjacent to one another in a horizontal arrangement. That is, the first indicia 36 is located adjacent to the second indicia 38, which is located adjacent to the third indicia 40, which is located adjacent to the fourth indicia 42, etc. In another embodiment, the sequence of icons or indicia may be disposed in a vertical arrangement or diagonal. In another embodiment, the sequence of icons may be disposed in an arched arrangement whereby the arch has a top portion at the apex of the curve and one indicia is highlighted at the top portion of the arch.

Still referring to FIG. 3, the line-up indicator 30 may also include a transitional indicator 60 disposed between the first indicia 36 and the second indicia 38. The transitional indicator 60 signals to the consumer a transition or progression from one level of whitening to the next level of whitening, for example, from the first level of whitening to the second level of whitening. Additional transitional indicators 60 may be disposed between the second indicia 38 and the third indicia 40 and between the third indicia 40 and the fourth indicia 42 and so on. While transitional indicator 60 is shown in FIG. 3 as dot, indicators of other symbols or shapes may also be used, if desired. The transitional indicator 60 further emphasizes the progressive nature of the various tooth-whitening strip article configurations.

The line-up indicator may also include a common color scheme that is associated with a particular level of whitening. The term "color," as used herein, relates to the phenomenon of visual perception that enables one to differentiate otherwise identical objects. In one embodiment, a background color scheme is chosen for the visual indicia 34 that matches a color scheme of various tooth-whitening strip article configurations. In one example, the visual indicia has a background color selected from pink, violet dark red, cyan, burgundy, silver, or combinations thereof. The use of a visual indicia color scheme that matches a color scheme of various tooth-whitening strip article configurations is used to facilitate consumers' identification and selection of the appropriate tooth-whitening strip article configuration for a particular user.

Similar to the line-up indicator 30, the power specific indicator 50 assists consumers in identifying the appropriate tooth-whitening strip article configuration for a particular user by associating each tooth-whitening strip article configuration with a corresponding level of whitening. As shown in FIGS. 1 and 2, the power specific indicator 50 includes a product name associating a product configuration with the particular level of whitening for which the product is designed. In one embodiment, the articles include a power specific indicator. In one embodiment, the power specific indicator comprises a product name associating the tooth-whitening strip article configuration with the corresponding whitening power.

For example, the first tooth-whitening strip article configuration could be named "GENTLE ROUTINE", while the second, third, fourth and fifth product configurations could be named "VIVID," "ADVANCED VIVID," "PROFESSIONAL EFFECTS," and "INTENSIVE PROFESSIONAL EFFECTS" respectively. Each of the product names listed are trademarks of tooth-whitening strip article products manufactured by The Procter and Gamble Company.

In yet another embodiment, a different power specific indicator 50 may be located below its corresponding indicia. For example, located below the first indicia 36 could be the name "GENTLE ROUTINE", while under the second, third, fourth and fifth indicia 38, 40, 42, and 44 could be named "VIVID," "ADVANCED VIVID," "PROFESSIONAL EFFECTS," and "INTENSIVE PROFESSIONAL EFFECTS" respectively.

In one embodiment, the line-up indicator further comprises a power specific indicator located in a substantially normal direction to the visual indicia to signal the particular tooth-whitening strip article configuration enclosed in the package. In one embodiment, the power specific indicator is selected from "gentle routine", "vivid", "advanced vivid", "advanced", "professional", "professional effects", "intensive treatment", "sensitive", "gentle", "mild", "advanced power", "touch-up", "express", and combinations thereof.

The package 10 may also include an informational corridor 80 disposed on the package 10. The informational corridor 80 further assists consumers in choosing the right product configuration matching a particular user's level of whitening.

Figure 4:
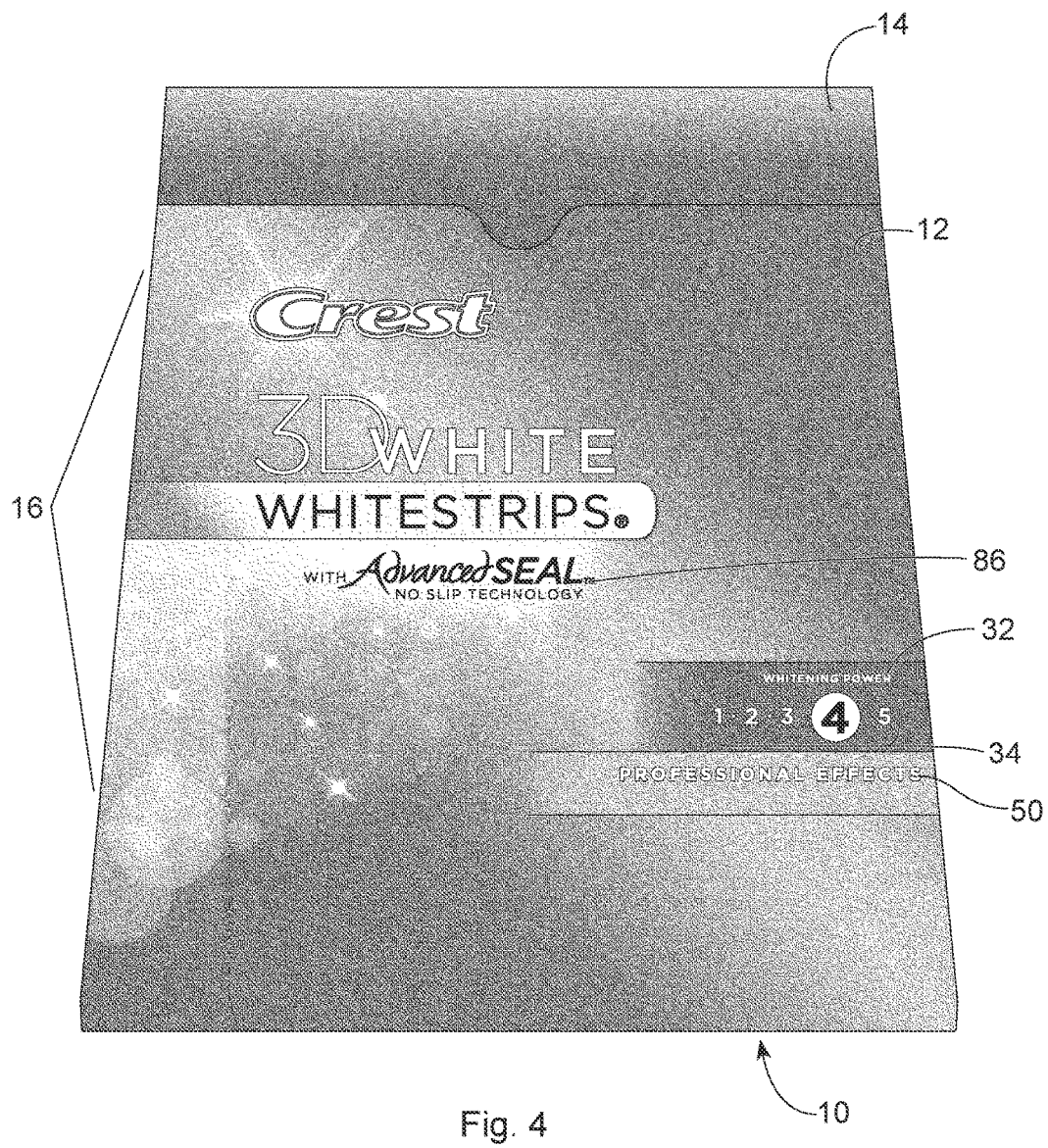
FIG. 4 illustrates an exemplary front panel of a package of tooth-whitening strip articles in accordance with one embodiment.
Figure 5:
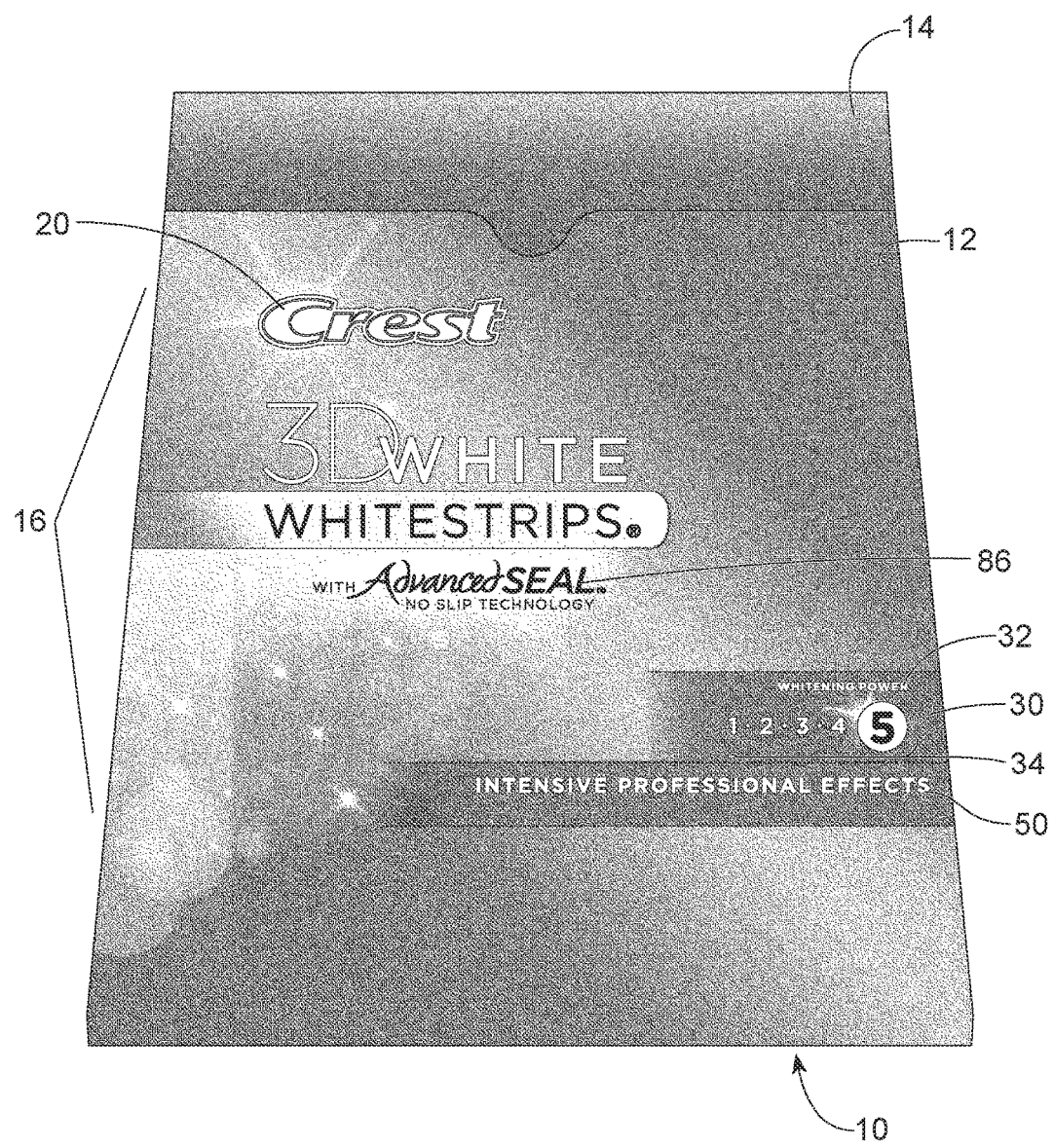
FIG. 5 illustrates an exemplary front panel of a package of tooth-whitening strip articles in accordance with one embodiment.

In the embodiment shown in FIG. 4, the at least one product benefit indicator 86 includes information-bearing indicia to convey the benefit associated with a particular tooth-whitening strip article configuration. The information-bearing indicia may include visual or narrative features or combinations thereof.

In one embodiment, the whitening power is selected from express power, advanced power, and combinations thereof.

In one embodiment, the first indicia depicts a first Arabic numeral corresponding to the first whitening power and the second indicia depicts a second Arabic numeral corresponding to the second whitening power. In another embodiment, the article includes a third indicia and the third indicia corresponds to a third whitening power, the third indicia being visibly different from the first and second indicia. In another embodiment, third indicia depicts a third Arabic numeral corresponding to the third whitening power. In another embodiment, the third whitening power comprises an advanced power. In another embodiment, the article further includes a fourth indicia, the fourth indicia corresponding to a fourth whitening power, the fourth indicia being visibly different from the first, second and third indicia. In another embodiment, the fourth indicia depicts a fourth Arabic numeral corresponding to the fourth whitening power. In another embodiment, the fourth whitening power comprises an express power.

In one embodiment, the narrative indicia comprise a sequence of Arabic numerals wherein one numeral is visually highlighted. In one embodiment, the one numeral is visually highlighted by having a larger font size than the other numerals in the sequence; by having a background color that is visibly distinct from the other numbers; by being visually highlighted by a graphic, or combinations thereof.

In one embodiment, the narrative indicia comprises a sequence of letters and/or numbers corresponding to a relative scale of whitening powers. In one embodiment, the narrative indicia is selected from the group consisting of "whitening power", "power level", "whitening strength", "whiteness level", "bleaching power", "peroxide level", "peroxide strength", "power", and combinations thereof.

In one embodiment, the line-up indicator comprises both at least one visual indicia and at least one narrative indicia and the visual indicia is located in a proximal relationship with the narrative indicia. In one embodiment, the first indicia is located adjacent to the second indicia.

In one embodiment, the article includes a transitional indicator disposed between the first and second indicia to signal a transition from the first whitening power to the second whitening power. Examples of transitional indicators useful herein include dots, arrows, stars, bullets, slashes, and combinations thereof. In one embodiment, the transitional indicator is a dot.

In one embodiment, the article includes an informational corridor disposed on the package, wherein the informational corridor includes at least one indicator selected from a number of treatments indicator, a number of strips indicator, a treatment time indicator, a product benefit indicator, and combinations thereof.

In one embodiment, the product benefit indicator comprises information-bearing indicia selected from the group consisting of stretchable, advanced seal, overnight, express whitening, advanced whitening, gentle formulation, professional effects, and superior seal.

Figure 6:
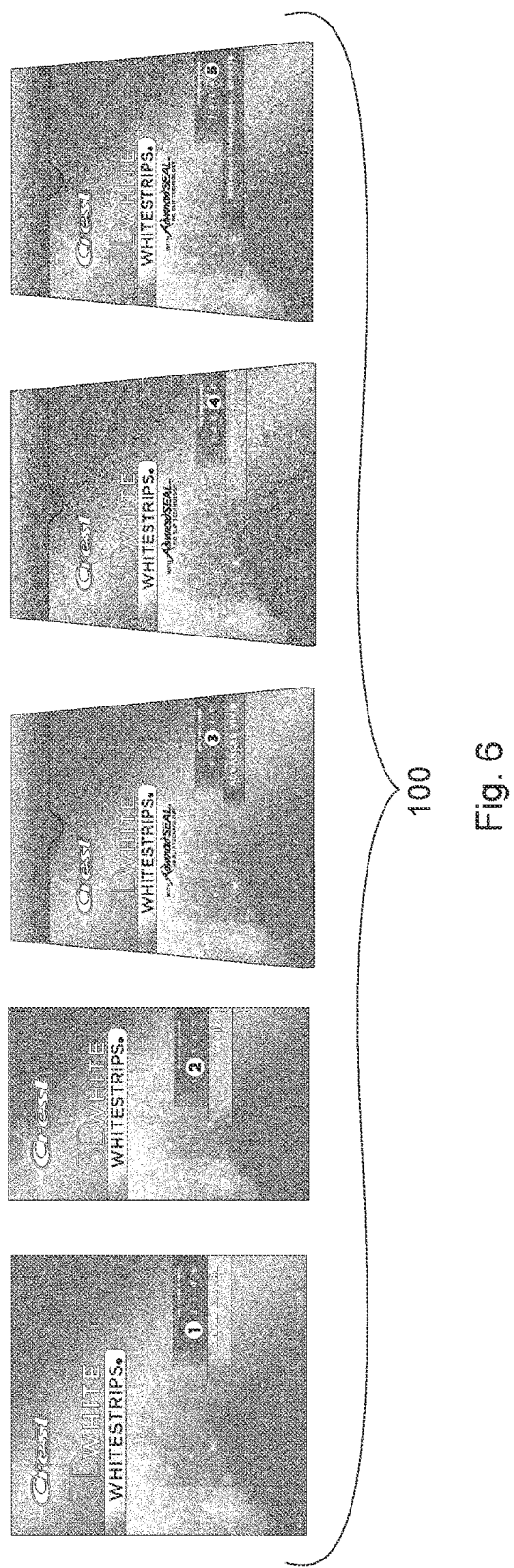
FIG. 6 illustrates an exemplary array of packages of tooth-whitening strip articles in accordance with one embodiment.

An array 100 of tooth-whitening strip article products according to the present invention is shown in FIG. 6. In one embodiment, the array including a tooth-whitening strip article of a first configuration corresponding to a user's first whitening power, the tooth-whitening strip article of the first configuration being enclosed in a first package; a tooth-whitening strip article of a second configuration corresponding to a user's second whitening power, the tooth-whitening strip article of the second configuration being enclosed in a second package; and a power communication system disposed on each of the first and second packages; the power communication system comprising a brand indicator; a line-up indicator wherein the line-up indicator comprises visual indicia and narrative indicia; and a power specific indicator; wherein the line-up indicator and power specific indicator associate the first and the second tooth-whitening strip article configurations with respective first and second whitening powers, the association enabling a consumer to identify the appropriate tooth-whitening strip article configuration for a user.

In one embodiment, the present invention relates to an array of tooth-whitening strip article products wherein the array further comprises: a tooth-whitening strip article of a third configuration corresponding to a user's third whitening power, the tooth-whitening strip article of the third configuration being enclosed in a third package; wherein the power communication system is disposed on each of the first, second and third packages; wherein the line-up indicator and power specific indicator associate the first, the second and the third tooth-whitening strip article configurations with respective first, second and third whitening powers, the association enabling a consumer to identify the appropriate tooth-whitening strip article configuration for a user.

In one embodiment, the present invention relates to an array of tooth-whitening strip article products wherein the array further comprises: a tooth-whitening strip article of a fourth configuration corresponding to a user's fourth whitening power, the tooth-whitening strip article of the fourth configuration being enclosed in a fourth package; wherein the power communication system is disposed on each of the first, second, third and fourth packages; wherein the line-up indicator and power specific indicator associate the first, the second, the third and the fourth tooth-whitening strip article configurations with respective first, second, third and fourth whitening powers, the association enabling a consumer to identify the appropriate tooth-whitening strip article configuration for a user.

In one embodiment, the present invention relates to an array of tooth-whitening strip article products wherein the array further comprises: at least one additional tooth-whitening strip article of an additional configuration corresponding to a user's additional whitening power, the tooth-whitening strip article of the additional configuration being enclosed in an additional package; wherein the power communication system is disposed on each of the packages; wherein the line-up indicator and power specific indicator associate the tooth-whitening strip article configurations with respective whitening powers, the association enabling a consumer to identify the appropriate tooth-whitening strip article configuration for a user.

In one embodiment, the present invention relates to a method of calculating a relative whitening power index for packaged oral care whitening strips, said method comprising the steps of:
  selecting a tooth-whitening strip comprising a composition comprising peroxide;
  evaluating a percentage level of peroxide in the composition;
  evaluating a number of the strips that will be packaged together to create a tooth-whitening strip kit;
  selecting a consumer strip wearing time period;
  multiplying the percentage level of peroxide by the number of the strips and then
  multiplying the result by the wearing time period to form a resulting whitening power level;
  assigning a power level index as follows;
    a. a first power level numerical range is assigned a first whitening power index;
    b. optionally, subsequent power level numerical ranges are assigned additional whitening power indices, wherein the additional whitening power indices have an incremental power level higher than the first whitening power index;

In one embodiment, the present invention relates to such a method wherein at least one subsequent power level numerical range is assigned an additional whitening power index.

In one embodiment, the present invention relates to such a method of calculating a relative whitening power level for packaged oral care whitening strips, said method comprising the steps of:

selecting at least one tooth-whitening strip kit comprising:
  i) an outer package;
  ii) at least one tooth-whitening strip contained within the package;
  iii) wherein the tooth-whitening strip comprises a composition comprising peroxide;
evaluating a percentage level of peroxide in the composition;
evaluating a number of the strips that will be contained within the tooth-whitening strip kit;
selecting a consumer strip wearing time period; multiplying the percentage level of peroxide by the number of the strips and then multiplying the result by the wearing time period to form a resulting whitening power level;
assigning a power level index as follows;
  i) a whitening power level range of from about 1 to about 15 is assigned a first whitening power index;
repeating the steps with one or more additional tooth-whitening strip kits;
displaying the power level index associated with the tooth-whitening strip kit on the outer package.

In one embodiment, the present invention relates to a method of assessing a whitening power index for packaged oral care whitening strips, said method comprising the steps of:
  selecting at least one tooth-whitening strip kit comprising:
    i) an outer package;
    ii) at least one tooth-whitening strip contained within the package;
    iii) wherein the tooth-whitening strip comprises a composition comprising peroxide;
  evaluating a percentage level of peroxide in the composition;
  evaluating a number of the strips that will be contained within the tooth-whitening strip kit;
  selecting a consumer strip wearing time period;
  multiplying the percentage level of peroxide by the number of the strips and then multiplying the result by the wearing time period to form a resulting whitening power level;
  assigning a power level index as follows;
    i) a whitening power level range of from about 1 to about 15 is assigned a first whitening power index;
    ii) a whitening power level range of from about 16 to about 30 is assigned a second whitening power index;
    iii) a whitening power level range of from about 31 to about 45 is assigned a third whitening power index;
  displaying the power level index associated with the tooth-whitening strip kit on the outer package.

In one embodiment, the present invention relates to a method of assessing a whitening power index for packaged oral care whitening strips, said method comprising the steps of:
  a) selecting a tooth-whitening strip comprising a composition comprising peroxide;
  b) evaluating a percentage level of peroxide in the composition;
  c) evaluating a number of the strips that will be packaged together to create a tooth-whitening strip kit;
  d) selecting a strip wearing time period;
  e) multiplying the percentage level of peroxide by the number of the strips and then multiplying the result by the wearing time period to form a resulting whitening power level; and
  f) assigning a power level index as follows;
    i) the whitening power level of from about 1 to about 15 is assigned a whitening power index of 1;
    ii) the whitening power level of from about 16 to about 30 is assigned a whitening power index of 2;
    iii) the whitening power level of from about 31 to about 45 is assigned a whitening power index of 3;
    iv) the whitening power level of from about 46 to about 60 is assigned a whitening power index of 4; and
    v) the whitening power level of greater than about 61 is assigned a whitening power index of 5.

In one embodiment, the present invention relates to a tooth-whitening strip kit including: a package; one or more tooth-whitening strip articles enclosed in the package comprising a composition; a brand indicator disposed on the package; d) a whitening power index disposed on the package; wherein the whitening power index is calculated as follows:
  evaluating a percentage level of peroxide in the composition;
  evaluating a number of the strips that will be contained within the kit;
  selecting a consumer strip wearing time period;
  multiplying the percentage level of peroxide by the number of the strips and then multiplying the result by the wearing time period to form a resulting whitening power level;
assigning a whitening power index as follows;
  a whitening power level range of from about 1 to about 15 is assigned a first whitening power index;
  a whitening power level range of from about 16 to about 30 is assigned a second whitening power index;
  a whitening power level range of from about 31 to about 45 is assigned a third whitening power index.
  a whitening power level range of from 46 to 60 is assigned a fourth whitening power index; and
  a whitening power level range of greater than 60 is assigned a fifth whitening power index.

Example I

Array of Packaged Tooth-Whitening Strip Articles

In an example according to the present invention, an array of packaged tooth-whitening strips is selected to provide consumers with a range of products having a range of whitening power indices. Each packaged product contains a number of whitening strips, instructions to consumers for the recommended time period to treat the teeth with each strip (in minutes) and a peroxide level in the whitening composition used in conjunction with the whitening strip.

Each package includes the brand indicator "CREST" (trademark of the Procter & Gamble Company, Cincinnati, Ohio, USA) in combination with the line-up indicator disposed therein on the front label.

|  | Whitening Power Index | | | | | |
| --- | --- | --- | --- | --- | --- | --- |
|  | 1 | 2 | 3 | 4 | 5 | 6 |
| Whitening Power Level Interval | 15 or less | 15-30 | 31-45 | 46-60 | 61-75 | >76 |

| Packaged Product | Line-Up Indicator | % Peroxide in Composition | # of Treatment Pouches in Package | Recommended Treatment Time (per treatment) | Resulting Whitening Power | Power Index |
|---|---|---|---|---|---|---|
| 1A | A | 5% | 25 | 5 | 7.5 | 1 |
| 1B | A | 10% | 25 | 5 | 12.5 | 1 |
| 1C | B | 10% | 10 | 30 | 30 | 2 |
| 1D | C | 9.5 | 15 | 30 | 42.75 | 3 |
| 1E | C | 10 | 4 | 120 | 48 | 3 |
| 1F | D | 10 | 20 | 30 | 60 | 4 |
| 1G | D | 10 | 10 | 60 | 60 | 4 |
| 1H | E | 10 | 7 | 90 | 63 | 5 |
| 1I | F | 10 | 8 | 120 | 96 | 6 |

Example II

Array of Packaged Tooth-Whitening Strip Articles

In an example according to the present invention, an array of packaged tooth-whitening strip articles is selected to provide consumers with a range of products having a range of whitening power indices. Each packaged product contains a number of whitening strips, instructions to consumers for the recommended time period to treat the teeth with each strip (in minutes) and a peroxide level in the whitening composition used in conjunction with the whitening strip. Consumer communication on the package provides the line-up indicator and stage specific indicator to provide consumers with the ability to select the right product for their needs.

Each package includes the brand indicator "CREST 3D WHITE" (trademark of the Procter & Gamble Company, Cincinnati, Ohio, USA) in combination with the line-up indicator disposed therein on the front label.

|  | Whitening Power Index | | | | | |
|---|---|---|---|---|---|---|
|  | 1 | 2 | 3 | 4 | 5 | 6 |
| Whitening Power Level Intervals | 15 or less | 15-30 | 31-45 | 46-60 | 61-75 | >76 |

Example III

Array of Packaged Tooth-Whitening Strip Products

In an example according to the present invention, an array of packaged tooth-whitening strips is selected to provide consumers with a range of products having a range of whitening power indices. Each packaged product contains a number of whitening strips, instructions to consumers for the recommended time period to treat the teeth with each strip (in minutes) and a peroxide level in the whitening composition used in conjunction with the whitening strip. Consumer communication on the package provides the line-up indicator and power specific indicator to provide consumers with the ability to select the right product for their needs.

Each package includes the brand indicator "CREST" (trademark of the Procter & Gamble Company, Cincinnati, Ohio, USA) in combination with the line-up indicator disposed therein on the front label.

|  | Whitening Power Index | | |
|---|---|---|---|
|  | 1 | 2 | 3 |
| Whitening Power Interval | 15 or less | 15-30 | >30 |

| Packaged Product | Line-Up Indicator | Power Specific Indicator | % Peroxide in Composition | # of Treatment Pouches in Package | Recommended Treatment Time (per treatment) | Resulting Whitening Power | Power Index |
|---|---|---|---|---|---|---|---|
| 2A | 1 | Gentle | 5% | 25 | 5 | 7.5 | 1 |
| 2B | 2 | Daily | 10% | 10 | 30 | 30 | 2 |
| 2C | 3 | 2 Hour | 10 | 4 | 120 | 48 | 3 |
| 2D | 4 | Daily Plus | 10 | 20 | 30 | 60 | 4 |
| 2E | 5 | Advanced | 10 | 7 | 90 | 63 | 5 |

| Packaged Product | Line-Up Indicator | Power Specific Indicator | % Peroxide in Composition | # of Treatment Pouches in Package | Recommended Treatment Time (per treatment) | Resulting Whitening Power | Power Index |
|---|---|---|---|---|---|---|---|
| 3A | I | Gentle | 5% | 25 | 5 | 7.5 | 1 |
| 3B | II | Daily | 10% | 10 | 30 | 30 | 2 |
| 3C | III | Advanced | 10 | 4 | 120 | 48 | 3 |

Example IV

Array of Packaged Tooth-Whitening Strip Articles

In an example according to the present invention, an array of packaged tooth-whitening strips is selected to provide consumers with a range of products having a range of whitening power indices. Each packaged product contains a number of whitening strips, instructions to consumers for the recommended time period to treat the teeth with each strip (in minutes) and a peroxide level in the whitening composition used in conjunction with the whitening strip.

Each package includes the brand indicators "CREST" and "WHITESTRIPS" (both trademarks of the Procter & Gamble Company, Cincinnati, Ohio, USA) in combination with the line-up indicator disposed therein on the front label.

| | Whitening Power Scale | | | | | |
|---|---|---|---|---|---|---|
| | 1 | 2 | 3 | 4 | 5 | 6 |
| Whitening Power Level Interval | 15 or less | 15-30 | 31-45 | 46-60 | 61-75 | >76 |

| Packaged Product | Line-Up Indicator | % Peroxide in Composition | # of Treatment Pouches in Package | Recommended Treatment Time (per treatment) | Resulting Whitening Power | Power Index |
|---|---|---|---|---|---|---|
| 4A | 1 | 5% | 25 | 5 | 7.5 | 1 |
| 4B | 1 | 10% | 25 | 5 | 12.5 | 1 |
| 4C | 2 | 10% | 10 | 30 | 30 | 2 |
| 4D | 3 | 9.5 | 15 | 30 | 42.75 | 3 |
| 4E | 3 | 10 | 4 | 120 | 48 | 3 |
| 4F | 4 | 10 | 20 | 30 | 60 | 4 |
| 4G | 4 | 10 | 10 | 60 | 60 | 4 |
| 4H | 5 | 10 | 7 | 90 | 63 | 5 |
| 4I | 6 | 10 | 8 | 120 | 96 | 6 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

Except as otherwise noted, the articles "a", "an", and "the" mean "one or more".

As used herein, "include(s)", "contain" or "comprising" means that other steps and other ingredients which do not affect the end result can be added. This term encompasses the terms "consisting of" and "consisting essentially of". The compositions and methods/processes of the present invention can contain, include, comprise, consist of, and consist essentially of the elements and limitations of the invention described herein, as well as any of the additional or optional ingredients, components, steps, or limitations described herein.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of calculating a relative whitening power index for packaged oral care whitening strips, said method comprising the steps of:
   a) selecting a tooth-whitening strip comprising a composition comprising peroxide;
   b) evaluating a percentage level of peroxide in the composition;
   c) evaluating a number of the strips that will be packaged together to create a tooth-whitening strip kit;
   d) selecting a consumer strip wearing time period;
   e) multiplying the percentage level of peroxide by the number of the strips and then multiplying the result by the wearing time period to form a resulting whitening power level;
   f) assigning a power level index as follows;

i) a first power level numerical range is assigned a first whitening power index;
ii) optionally, subsequent power level numerical ranges are assigned additional whitening power indices, wherein the additional whitening power indices have an incremental power level higher than the first whitening power index;

wherein said whitening strips used in said method are prepared by combining a whitening composition comprising peroxide with a backing layer.

2. A method of calculating a relative whitening power level for packaged oral care whitening strips, said method comprising the steps of:
   a) selecting at least one tooth-whitening strip kit comprising:
      i) an outer package;
      ii) at least one tooth-whitening strip contained within the package;
      iii) wherein the tooth-whitening strip comprises a composition comprising peroxide;
   b) evaluating a percentage level of peroxide in the composition;
   c) evaluating a number of the strips that will be contained within the tooth-whitening strip kit;
   d) selecting a consumer strip wearing time period;
   e) multiplying the percentage level of peroxide by the number of the strips and then multiplying the result by the wearing time period to form a resulting whitening power level;
   f) assigning a power level index as follows;
      i) a whitening power level range of from about 1 to about 15 is assigned a first whitening power index;
   g) repeating steps a through f with one or more additional tooth-whitening strip kits;
   h) displaying the power level index associated with the tooth-whitening strip kit on the outer package;

wherein said whitening strips used in said method are prepared by combining a whitening composition comprising peroxide with a backing layer.

3. A method of assessing a whitening power index for packaged oral care whitening strips, said method comprising the steps of:
   a) selecting at least one tooth-whitening strip kit comprising:
      i) an outer package;
      ii) at least one tooth-whitening strip contained within the package;
      iii) wherein the tooth-whitening strip comprises a composition comprising peroxide;
   b) evaluating a percentage level of peroxide in the composition;
   c) evaluating a number of the strips that will be contained within the tooth-whitening strip kit;
   d) selecting a consumer strip wearing time period;
   e) multiplying the percentage level of peroxide by the number of the strips and then multiplying the result by the wearing time period to form a resulting whitening power level;
   f) assigning a power level index as follows;
      i) a whitening power level range of from about 1 to about 15 is assigned a first whitening power index;
      ii) a whitening power level range of from about 16 to about 30 is assigned a second whitening power index;
      iii) a whitening power level range of from about 31 to about 45 is assigned a third whitening power index;
   g) displaying the power level index associated with the tooth-whitening strip kit on the outer package;

wherein said whitening strips used in said method are prepared by combining a whitening composition comprising peroxide with a backing layer.

* * * * *